United States Patent [19]

Hoelderich et al.

[11] Patent Number: 4,788,326
[45] Date of Patent: * Nov. 29, 1988

[54] PREPARATION OF 4-PENTENOATES

[75] Inventors: Wolfgang Hoelderich, Frankenthal; Wolfgang Richter, Wachenheim; Hubert Lendle, Ludwigshafen; Klaus-Dieter Malsch, Schifferstadt, all of Fed. Rep. of Germany

[73] Assignee: BASF Aktiengesellschaft, Fed. Rep. of Germany

[*] Notice: The portion of the term of this patent subsequent to Sep. 20, 2005 has been disclaimed.

[21] Appl. No.: 870,121

[22] Filed: Jun. 3, 1986

[30] Foreign Application Priority Data

Jun. 14, 1985 [DE] Fed. Rep. of Germany ....... 3521381

[51] Int. Cl.$^4$ ............................................. C07C 67/333
[52] U.S. Cl. .................................................... 560/205
[58] Field of Search .......................... 560/205; 585/666

[56] References Cited

U.S. PATENT DOCUMENTS

| 3,804,746 | 4/1974 | Chu | 585/666 |
| 4,332,966 | 6/1982 | Isogai et al. | 560/206 |
| 4,401,637 | 8/1983 | Marosi et al. | 423/329 |
| 4,529,815 | 7/1985 | Schneider et al. | 560/205 |

Primary Examiner—Michael L. Shippen
Attorney, Agent, or Firm—Keil & Weinkauf

[57] ABSTRACT

4-Pentenoates are prepared by isomerization by a process in which isomeric pentenoates are treated with a zeolite of the pentasil type at from 50° to 300° C., and the 4-pentenoate is distilled off from the reaction mixture.

11 Claims, No Drawings

PREPARATION OF 4-PENTENOATES

In the preparation of pentenoates by reacting butadiene with carbon monoxide and an alcohol in the presence of a metal carbonyl catalyst, as described in, for example, German Laid-Open Application No. 3,040,432, substantial amounts of isomeric pentenoates are obtained. However, for further reactions, for example for the preparation of δ-formylvalerates by hydroformylation of pentenoates, 4-pentenoates are preferred starting compounds. Attempts have therefore been made to obtain 4-pentenoates by isomerization of isomeric pentenoates. However, Bull. Chem. Soc. Japan, 46, 528 discloses that the isomerization of methyl 3-pentenoate in the presence of a cobalt carbonyl gives predominantly methyl 2-pentenoate. In another procedure described in Tetrahedron 28 (1972), 5769–5777, it is possible, in the presence of a complex of rhodium-triphenylphosphine and tin chloride, to shift the equilibrium in the isomerization so that 4-pentenoates are obtained. However, the catalyst used in this procedure is deactivated in the course of a few hours.

European Patent Application No. 226,349 describes a process for the preparation of 4-pentenoates from a mixture of pentenoates by treatment with an acidic zeolite which contains palladium, ruthenium or rhodium.

In the isomerization of pentenoates, five isomers, i.e. the 4-pentenoate, the cis- and trans-3-pentenoates and the cis- and trans-2-pentenoates, are present when thermodynamic equilibrium is reached, the equilibrium being shifted strongly toward the trans-2-pentenoate.

It is an object of the present invention to provide a process for the preparation of 4-pentenoates from isomeric pentenoates, in which the catalyst used has a long life and is easy to regenerate, the linear displacement of the double bond to give the 4-pentenoate takes place preferentially and furthermore the cis-2-pentenoate, which is difficult to separate off, is formed in a very small amount.

We have found that this object is achieved by a process for the preparation of 4-pentenoates by isomerization, in which isomeric pentenoates are treated with a zeolite at elevated temperatures and the 4-pentenoate is distilled off from the reaction mixture, wherein a zeolite of the pentasil type is used.

The novel process has the advantage that the pentasil zeolite used preferably permits only a linear displacement of the double bond to give the 4-pentenoates, and the formation of cis-2-pentenoates is virtually completely suppressed. Other advantages of the novel process are that the pentasil zeolites used have a fairly long life, can more easily be regenerated without any loss of activity and catalyze the linear displacement of the double bond to give the 4-pentenoates even without the addition of catalytically active metals. Furthermore, the reaction mixture obtained is easier to separate by distillation.

Advantageously used starting materials are isomeric pentenoates, for example 2- or 3-pentenoates, which are derived from alcohols of not more than 12 carbon atoms. Isomeric alkyl pentenoates, in particular pentenoates of alcohols of not more than 4 carbon atoms, are particularly preferably used. Examples of suitable starting materials are methyl 3-pentenoate, ethyl 3-pentenoate, propyl 3-pentenoate, butyl 3-pentenoate, methyl 2-pentenoate, ethyl 2-pentenoate and propyl 2-pentenoate. Mixtures of isomeric pentenoates, as obtained in the reaction of butadiene with carbon monoxide and alcohols in the presence of metal carbonyls as described in German Laid-Open Application DOS No. 3,040,432, are also useful. 3-Pentenoates are particularly preferred.

The zeolites are crystalline aluminosilicates which possess a highly ordered structure comprising a rigid three-dimensional network of $SiO_4$ and $AlO_4$ tetrahedra which are bonded by common oxygen atoms. The ratio of silicon and aluminum atoms to oxygen is 1:2. The electrovalency of the aluminum-containing tetrahedra is compensated by inclusion of cations in the crystal, for example an alkali metal ion or hydrogen ion. Cation exchange is possible. Prior to dehydration by drying or calcination, the voids between the tetrahedra are occupied by water molecules.

Zeolites are divided into different groups, depending on their structure (cf. Ullmanns Encyclopädie der technischen Chemie, 4th edition, volume 24, page 575 (1983)). For example, in the mordenite group the zeolite structure is formed by chains, and in the chabasite group it is formed by layers of tetrahedra, whereas in the faujasite group the tetrahedra are arranged to form polyhedra, for example a cubooctahedron, which is composed of four-membered and six-membered rings. Depending on the way in which the cubooctahedra are linked, giving cavities and pores of different sizes, a distinction is made between zeolites of types A, X and Y.

In the novel process, the catalysts used are zeolites of the pentasil type, all of which possess, as a basic building block, a five-membered ring composed of $SiO_4$ tetrahedra. They have a high ratio of $SiO_2$ to $Al_2O_3$ and pore sizes between those of the zeolites of type A and those of type X or Y (cf. Ullmanns Encyclopädie der technischen Chemie, 4th edition, Vol. 24, 1983).

The zeolites used may differ in composition and may be aluminosilicate, borosilicate, iron silicate, gallium silicate, chromium silicate, arsenosilicate or bismuth silicate zeolites or mixtures of these, and aluminogermanate, borogermanate, gallium germanate and iron germanate zeolites or mixtures of these. The isotactic zeolites which are described in German Laid-Open Application DOS No. 3,006,471 may be mentioned particularly.

The aluminosilicate, borosilicate and iron silicate zeolites of the pentasil type are particularly useful for isomerization of the pentenoates. The aluminosilicate zeolite is prepared, for example, from an aluminum compound, preferably aluminum hydroxide or aluminum sulfate, and a silicon component, preferably finely divided silica, in an aqueous amine solution, in particular in 1,6-hexanediamine, 1,3-propanediamine or triethylenetetramine solution, with or without the addition of an alkali or alkaline earth, at from 100° to 220° C. under autogenous pressure. The aluminosilicate zeolites obtained have a ratio of $SiO_2$ to $Al_2O_3$ of from 10 to 40,000, in particular from 30 to 1000, depending on the amounts of starting materials selected. Aluminosilicate zeolites of this type may also be synthesized in an ether medium, such as diethylene glycol dimethyl ether, in an alcoholic medium, such as methanol or 1,4-butanediol, or in water.

The borosilicate zeolite is synthesized, for example, at from 90° to 200° C. under autogenous pressure, by reacting a boron compound, such as boric acid, with a silicon compound, preferably finely divided silica, in an aqueous amine solution, in particular in 1,6-hexanediamine, 1,3-propanediamine or triethylenetetramine solution, with or without the addition of an alkali or alkaline earth. Such borosilicate zeolites can also be obtained if the reaction is carried out in an ether solution, e.g. diethylene glycol dimethyl ether, or in alcoholic solution, e.g. 1,6-hexanediol, instead of in an aqueous amine solution.

The iron silicate zeolite is obtained, for example, from an iron compound, preferably iron(III) sulfate, and a silicon compound, preferably finely divided silica, in an aqueous amine solution, in particular in 1,6-hexanediamine, with or without the addition of an alkaline earth, at from 100° to 200° C. under autogenous pressure.

The aluminosilicate, borosilicate or iron silicate zeolites prepared in this manner are isolated, dried, as a rule at from 100° to 160° C., preferably from 110° to 130° C., calcined at from 450° to 550° C., in particular from 490° to 530° C., and then converted to extrudates or tablets together with a binder in a weight ratio of from 90:10 to 40:60. Suitable binders are aluminas, preferably boehmite, finely divided alumina, amorphous aluminosilicates having a ratio of $SiO_2$ to $Al_2O_3$ of from 25:75 to 90:10, preferably 75:25, silica, preferably finely divided silica, mixtures of finely divided silica and finely divided alumina, finely divided titanium dioxide, and clay. After the molding procedure, the extrudates or tablets are advantageously dried at from 100° to 160° C. for not more than 16 hours and then calcined at from 450° to 550° C. for not more than 24 hours.

Advantageous catalysts are also obtained if the aluminosilicate, borosilicate or iron silicate zeolites isolated are molded directly after drying, and are calcined only after the molding procedure. The novel aluminosilicate, borosilicate or iron silicate zeolites can, however, also be used in pure form, without a binder, as extrudates or tablets. In this case, molding is carried out with the addition of extrudation assistants or peptization agents, such as hexaethylcellulose, stearic acid, potato starch, formic acid, acetic acid, oxalic acid, nitric acid, ammonia, amines, silicoesters, graphite or mixtures of these.

If, because of the method of preparation, the zeolites are not in the preferred acidic H form but in, for example, the Na form, the latter can advantageously be converted completely or partially to the H form by ion exchange with ammonium ions followed by calcination, or by treatment with an acid.

If, when the zeolite catalysts are used according to the invention, deactivation due to coking occurs, it is advisable to regenerate the zeolites by burning off the coke deposit with air or with a mixture of air and nitrogen at from 400° to 550° C., preferably from 490° to 550° C. As a result of this, the zolites regain their initial activity.

The zeolites used according to the invention advantageously contain alkali metal ions, such as sodium ions, and/or alkaline earth metal ions, such as calcium or magnesium ions. The zeolite may be provided with the content of alkali metal and/or alkaline earth metal ions at as early a stage as the synthesis, by an appropriate choice of starting materials, or the content of the said ions may be introduced into the ready-prepared zeolites by ion exchange or by impregnation with the appropriate metal salts. The content of alkali metal and/or alkaline earth metal ions is advantageously from 0.05 to 3.5% by weight, based on the zeolite.

It has also proved useful for the pentasil zeolites used according to the invention to contain metals of group VIII of the periodic table. Examples of preferred metals are cobalt, iron and nickel, as well as noble metals, such as palladium, platinum, rhodium, ruthenium or osmium. The content of the above metals is preferably from 0.1 to 7.0, particularly preferably from 0.5 to 3.5, % by weight, based on the zeolite. The transition metals are advantageously introduced into the zeolite used by initially taking the molded zeolite in a riser tube and passing over an aqueous and/or amine-containing solution of a halide or nitrate of the stated metals at from 20° to 100° C. Ion exchange of this type is carried out on, for example, the hydrogen, ammonium or alkali metal form of the zeolite. In another possible method for applying the metal to the zeolite, the zeolite material is impregnated, for example with a halide, a nitrate or an oxide of the transition metals in aqueous and/or alcoholic and/or amine-containing solution. Both ion exchange and impregnation are followed by one or more drying steps and, if desired, also repeated calcination.

It is also advantageous for the catalysts to contain, for example, from 0.1 to 4, preferably from 0.5 to 2.5, % by weight of rare earth metals, in particular cerium and/or lanthanum.

In a possible embodiment, for example, cobalt nitrate, cerium nitrate or lanthanum nitrate is dissolved in water, and the molded or unmolded zeolite is impregnated with this solution for a considerable time, as a rule not more than 30 minutes. Thereafter, the excess water is removed in a rotary evaporator, and the impregnated zeolite is then dried at from 100° to 160° C. and calcined at from 450° to 550° C. This impregnation process may be repeated several times in succession until the desired metal content is obtained.

In another procedure, the pure zeolite powder is suspended in an aqueous cobalt nitrate solution or ammoniacal palladium nitrate solution and treated for from 2 to 24 hours at from 40° to 100° C. After it has been filtered off, dried at from 100° to 160° C. and calcined at from 450° to 550° C., the zeolite doped in this manner is converted to extrudates or pellets, with or without a binder.

The zeolite present in the H form or ammonium form can be subjected to ion exchange, for example, as follows: the zeolite which has been molded with or without a binder. and is in the form of extrudates or pellets is initially taken in a column, and, for example, an aqueous cerium nitrate solution or cobalt nitrate solution is circulated over the said zeolite at from 30° to 80° C. for from 15 to 20 hours. The zeolite is then washed thoroughly with water, dried and calcined. Ion exchange of this type may also be carried out using ammoniacal palladium nitrate solution.

It has proven useful to treat zeolites containing a metal, in particular those containing a noble metal, with hydrogen at from 200° to 550° C., for example for from 1 to 5 hours. Before the treatment with hydrogen, the catalyst is advantageously slowly heated to not more than 300° C. in the presence of molecular oxygen or of a gas containing this. It is also advantageous if the hydrogen used contains olefins of 2 to 4 carbon atoms.

In another possible method of modification, the molded or unmolded zeolite is treated with an acid, such as hydrochloric acid, hydrofluoric acid or phosphoric acid, and/or with steam. By precoking, it is also possible to adjust the activity of the catalyst to achieve optimum selectivity in respect of the desired reaction product.

The novel zeolites of the pentasil type may alternatively be used in the form of 2–4 mm extrudates, tablets having a diameter of from 3 to 5 mm, powders having a particle size of from 0.1 to 0.5 mm, or fluidizable material.

The isomerization is advantageously carried out at from 50° to 300° C., as a rule under atmospheric pressure, reduced pressure or superatmospheric pressure, for example up to 50 bar.

In a batchwise procedure, zeolite powder is suspended in the mixture of isomeric pentenoates, for example in a stirred container, and the suspension is stirred at from 50° to 250° C., in particular from 100° to 200° C., for from 2 to 20 hours. The catalyst is then separated off, after which methyl 4-pentenoate is isolated by distillation.

In a preferred, continuous procedure, a molded zeolite of the pentasil type is initially taken in a reaction tube, and the mixture of isomeric pentenoates which is to be isomerized is pumped in liquid form through the tube at from 50° to 250° C., in particular from 100° to 200° C., preferably from 100° to 150° C., the mean residence time being from 5 to 100 minutes. The reaction mixture is then separated by a conventional method, for example by distillation, and unconverted starting materials are advantageously recycled.

In a particularly preferred embodiment of the novel process, the isomeric pentenoates are passed in gaseous form, if appropriate together with an inert carrier gas, such as nitrogen, over the novel zeolite of the pentasil type. In this procedure, a temperature of from 150° to 300° C., in particular from 150° to 250° C., is advantageously maintained. It has proven useful to maintain a space velocity (WHSV; grams of starting mixture per gram of catalyst per hour) of from 0.1 to 20, in particular from 0.5 to 5, $h^{-1}$. The gaseous reaction mixture obtained is condensed, and methyl 4-pentenoate is obtained by distillation.

4-Pentenoates obtainable by the novel process are useful for the preparation of δ-formylvalerates, which are intermediates for the preparation of ε-caprolactam, hexanediol or adipic acid.

The Examples which follow illustrate the process.

Catalyst A

An aluminosilicate zeolite of the pentasil type was prepared under hydrothermal conditions, under autogenous pressure and at 150° C., from 650 g of finely divided $SiO_2$ and 203 g of $Al_2(SO_4)_3 \cdot 18\ H_2O$ in 10 kg of an aqueous 1,6-hexanediamine solution (weight ratio 50:50) in a stirred autoclave. The crystalline reaction product was filtered off, washed thoroughly, dried at 110° C. for 24 hours and calcined at 500° C. This aluminosilicate zeolite contained 92.8% by weight of $SiO_2$ and 4.2% by weight of $Al_2O_3$.

Catalyst A was obtained by molding this aluminosilicate zeolite with boehmite in a weight ratio of 60:40 to give 2 mm extrudates, which were dried at 110° C. for 16 hours and calcined at 500° C. for 16 hours.

Catalyst B

The zeolite was prepared in a hydrothermal synthesis from 640 g of $SiO_2$ (finely divided silica), 122 g of $H_3BO_3$, 8000 g of an aqueous hexanediamine solution (weight ratio 50:50) at 170° C. under autogenous pressure in a stirred autoclave. The crystalline reaction product was filtered off, washed thoroughly, dried at 100° C. for 24 hours and calcined at 500° C. for 24 hours. The resulting borosilicate zeolite of the pentasil type contained 94.2% by weight of $SiO_2$ and 2.3% by weight of $B_2O_3$.

Catalyst B was obtained by molding this borosilicate zeolite with boehmite in a weight ratio of 60:40 to give 2 mm extrudates, which were dried at 110° C. for 16 hours and calcined at 500° C. for 16 hours.

Catalyst C

Catalyst C was prepared in the same way as catalyst B, except that, instead of boehmite, finely divided $Al_2O_3$ was used as the extrudation binder.

Catalyst D

By treating catalyst B with 20% strength $NH_4Cl$ solution in a weight ratio of 1:15 at 80° C. for 2 hours and then subjecting the product to ion exchange with an ammoniacal $Pd(NH_3)_4(NO_3)_2$ solution at 50° C., catalyst D was obtained. After drying at 110° C. and calcination at 500° C. for 5 hours, this catalyst had a Pd content of 0.8% by weight.

Catalyst E

Catalyst E was prepared in the same way as catalyst D, but had a Pd content of 3.3% by weight.

Catalyst F

Catalyst F was obtained by converting the borosilicate zeolite powder described under catalyst B to 2 mm extrudates without the addition of a binder, drying the extrudates at 110° C., calcining them at 500° C. for 16 hours and then treating them with 20% strength $NH_4Cl$ solution in a weight ratio of 1:15 at 80° C. for 2 hours, subjecting these treated extrudates to ion exchange with an ammoniacal $Pd(NH_3)_4(NO_3)_2$ solution at 50° C. and then drying the product at 110° C. and calcining it at 500° C. for 5 hours. Catalyst F contained 2.1% by weight of Pd.

Catalyst G (comparison)

The catalyst used was a Y zeolite laden with 0.5% by weight of palladium as described in EP-A-126 349.

Isomerization

The experimental results obtained with the catalysts described above are summarized in Table 1. Methyl 3-pentenoate was chosen as the starting material.

The reactions were carried ot in the gas phase under isothermal conditions in a helical tube reactor having an internal diameter of 0.6 cm and a length of 90 cm for not less than 6 hours. The reaction products were isolated by a conventional method and characterized. The products and the starting materials were determined quantitatively by gas chromatography.

EXAMPLE 8

30 ml/hour of methyl 3-pentenoate were converted in the course of 120 hours at 180° C. over catalyst E in a reactor charged with 80 g of catalyst. The content of 4-pentenoate in the product mixture, which was initially 8.8% by weight, fell to 6.5% by weight during this time.

COMPARATIVE EXAMPLE 2

The procedure described in Example 8 was followed, except that catalyst G was used. Under the same reaction conditions, the content of 4-pentenoate fell from 10.7% by weight to 6.7% by weight after only 6 hours.

TABLE 1

| | Example | | | | | | | Comparison |
|---|---|---|---|---|---|---|---|---|
| | 1 | 2 | 3 | 4 | 5 | 6 | 7 | 1 |
| Isomerization of methyl 3-pentenoate (3-PAE) | | | | | | | | |
| Catalyst | A | B | C | D | E | E | F | G |
| Temperature | 180° C. | 180° C. | 180° C. | 180° C. | 180° C. | 180° C. | 180° C. | 180° C. |
| WHSV | 2 h$^{-1}$ | 1 h$^{-1}$ | 1 h$^{-1}$ | 1.4 h$^{-1}$ | 1 h$^{-1}$ | 2 h$^{-1}$ | 2.5 h$^{-1}$ | 2 h$^{-1}$ |
| Product composition, % by weight | | | | | | | | |
| 4-PAE | 3.5 | 3.7 | 5.1 | 8.0 | 9.8 | 8.8 | 9.9 | 10.7 |
| 3-PAE | 94.9 | 93.8 | 92.4 | 86.9 | 82.2 | 86.2 | 85.4 | 75.3 |
| trans-2-PAE | 1.6 | 2.5 | 2.5 | 3.7 | 8.0 | 4.8 | 4.7 | 13.1 |
| cis-2-PAE | — | — | — | 0.4 | — | — | — | 0.9 |

We claim:

1. A process for the preparation of 4-pentenoic esters by the isomerization of 3-pentenoic esters which comprises:

heating 3-pentenoic esters in a reactor to a temperature of from 50° C. to 300° C. in the presence of a zeolite catalyst having a pentasil structure, and distilling off from the reaction mixture the 4-pentenoic esters that are formed.

2. The process of claim 1, wherein an aluminosilicate zeolite is used.

3. The process of claim 1, wherein a borosilicate zeolite is used.

4. The process of claim 1, wherein an iron silicate zeolite is used.

5. The process of claim 1, wherein the zeolite contains a metal of group VIII of the periodic table.

6. The process as claimed in claim 1, wherein the zeolite of the pentasil type contains palladium, platinum and/or rhodium.

7. The process of claim 1, wherein the zeolite of the pentasil type contains cobalt and/or nickel.

8. The process of claim 1, wherein the zeolite of the pentasil type contains from 0.1 to 7.0% by weight of metal.

9. The process of claim 1, wherein the zeolite of the pentasil type contains alkali metal and/or alkaline earth metal ions.

10. The process of claim 1, wherein the zeolite of the pentasil type contains a rare earth metal.

11. The process of claim 1, wherein the zeolite of the pentasil structure contains palladium.

* * * * *